United States Patent [19]
Adams

[11] Patent Number: 5,641,326
[45] Date of Patent: Jun. 24, 1997

[54] METHOD AND APPARATUS FOR INDEPENDENT ATRIAL AND VENTRICULAR DEFIBRILLATION

[75] Inventor: Theodore P. Adams, Edina, Minn.

[73] Assignee: Angeion Corporation, Plymouth, Minn.

[21] Appl. No.: 166,219

[22] Filed: Dec. 13, 1993

[51] Int. Cl.⁶ ........................................................ A61N 1/39
[52] U.S. Cl. .................................................. 607/5; 607/123
[58] Field of Search ............................... 607/5, 123, 122, 607/119

[56] References Cited

U.S. PATENT DOCUMENTS

| 3,942,536 | 3/1976 | Mirowski et al. | |
|---|---|---|---|
| 4,603,705 | 8/1986 | Speicher et al. | |
| 4,727,877 | 3/1988 | Kallok | 607/5 |
| 4,817,608 | 4/1989 | Shapland et al. | |
| 5,111,811 | 5/1992 | Smits | 607/129 |
| 5,165,403 | 11/1992 | Mehra | 607/5 |
| 5,269,319 | 12/1993 | Schulte et al. | 607/123 |

OTHER PUBLICATIONS

Document Number 07/919233 Date Jul. 7, 1992 Name Anderson et al.
Document Number 08/096170 Date Jul. 22, 1993 Name Adams et al.

Primary Examiner—William E. Kamm
Assistant Examiner—Kennedy J. Schaetzle
Attorney, Agent, or Firm—Patterson & Keough, P.A.

[57] ABSTRACT

The invention discloses a catheter for use with an implantable cardioverter in which the catheter has at least two discharge electrodes positioned along the length of the catheter in such a fashion as to place each electrode in the optimal position to effect atrial and ventricular cardioversion and defibrillation.

7 Claims, 7 Drawing Sheets

METHOD AND APPARATUS FOR INDEPENDENT ATRIAL AND VENTRICULAR DEFIBRILLATION

CROSS REFERENCES TO CO-PENDING APPLICATIONS

This patent application is related to the following; to co-pending U.S. Patent Application entitled IMPLANTABLE CARDIOVERTER DEFIBRILLATOR SYSTEM HAVING INDEPENDENTLY CONTROLLABLE ELECTRODE DISCHARGE PATHWAY, Ser. No. 08/096,170, filed Jul. 22, 1993, and assigned to the same assignee of the present invention, a copy of which is attached and the disclosure of which is hereby incorporated by reference; and to co-pending U.S. Patent Application entitled LOW PROFILE DEFIBRILLATION CATHETER, Ser. No. 07/919,233, Jul. 7, 1992, now U.S. Pat. No. 5,433,743, and assigned to the same assignee of the present invention, a copy of which is attached and the disclosure of which is hereby incorporated by reference.

FIELD OF THE INVENTION

The present invention relates generally to cardioversion defibrillator electrode catheters and in particular to an implantable intravascular intracardiac catheter bearing discharge electrodes optimized in terms of anatomic placement within the heart.

BACKGROUND OF THE INVENTION

The last several decades have seen considerable advancement in the treatment of cardiac dysrhythmias encountered in the course of heart disease. Particularly dramatic results have been achieved in the treatment for ventricular fibrillation, the most serious form of cardiac dysrhythmia. Early cardiac defibrillation systems were externally applied and, as the efficacy of the system was proven, efforts focused on providing increasingly smaller defibrillation systems that would be suitable for implantation. Along with the advancement of electrical intervention to treat defibrillation, electrical treatment of other ventricular and atrial dysrhythmias was undertaken. Experience has now demonstrated that many cardiac dysrhythmias are amenable to treatment by electrical countershock intervention.

Examples of the various types of cardiac dysrhythmias are ventricular fibrillation, ventricular flutter, high rate ventricular tachycardia, low rate ventricular tachycardia, supraventricular tachycardias including atrial fibrillation and atrial flutter. These and other dysrhythmias have been demonstrated to be treatable by application of an electrical countershock of appropriate energy, size, and waveform such as to correct the cardiac dysrhythmia thereby converting the rhythm to a normal sinus rhythm or a rhythm of lesser morbidity.

Necessary components of any defibrillation system are the discharge electrodes used to deliver an electrical countershock to the myocardium. The very first defibrillation devices were external devices that utilized large patch or disc electrodes applied to the surface of the patient's skin, generally with one electrode at or near the low left antero-lateral aspect of the chest and the second electrode placed well up over the sternum or into the right upper anterior chest wall. An electrical countershock up to 400 Joules was then delivered between these two electrodes.

As implantable defibrillator devices have been developed, electrodes have been devised to allow for implantation within the patient's body, in and around the heart. The implantation of internal electrodes is obviously more complicated than the placement of external electrodes. The complexity of the surgical procedure required to implant the electrodes is closely associated with the degree of complexity for any given electrode configuration.

Several early internal electrodes required major surgery in the form of a thoracotomy to open the chest and place patch electrodes either on the pericardium or further opening the pericardium and placing electrodes directly onto the epicardial surface of the heart. The electrode leads are then tunneled out to an implanted device that usually needs to be implanted within the abdominal cavity due to the excessive size of the implantable cardioverter defibrillator (ICD).

Alternative patch electrode configurations have been developed in the form of electrodes suitable for implantation within the subcutaneous space of a patient. Ideal locations for placement of these subcutaneous patch electrodes has been in the left antero-lateral chest wall outside the rib cage proper. The metallic surface covering of an ICD housing is useful as an alternative subcutaneous electrode. Further development and refinement of ICDs have allowed attainment of sizes small enough to allow for comfortable implantation within a subcutaneous pocket in the infraclavicular space of the anterior chest wall. Convenience of implantation within the infraclavicular space allows for ready access to the venous vascular system via the subclavian veins.

The convenience of vascular access has seen a development in the art for intravascular catheters bearing one to several electrodes suitable for discharge into the myocardium. The arrangement is not unlike that arrangement used for cardiac pacemakers. The significant difference between ICD systems and cardiac pacemakers is the amount of energy delivered. Electrical cardioversion in general, and ventricular defibrillation in particular, can require upwards of 40 Joules of energy to be delivered over a 3 to 10 millisecond duration through the intravascular discharge electrodes. Initial peak currents can range as high as 25 to 30 amps and initial voltages are as high as 750 volts. Given this amount of energy, the practice has been to manufacture discharge electrodes with sufficient surface area so as to provide an electrical field density sufficiently low to avoid burning the immediately adjacent myocardial tissue.

The application of an electrical countershock depends in some part on the actual myocardial dysrhythmia detected. In general, the efficacy of any electrical countershock therapy will be directly dependent upon how well the myocardium is immersed within the electrical field generated by the countershock. For example, epicardial patches that have been positioned on the external surface of the myocardium must be positioned carefully to ensure that the space between the margins of the patches is uniform. Any position closer than another position will allow shunting of current at that localized position increasing the electrical field density in a focal fashion which may contribute to focal damage in that area and lack of treatment in the rest of the myocardium. With intravascular catheters significant impairment of electrical treatment is seen where countershock energy has shunted through the blood itself from the edge of one countershock electrode to the edge of the nearest adjacent countershock electrode. Such shunted countershock energy does not enter the myocardium and treatment efficacy deteriorates. Because of this phenomenon, the practice has been to employ discharge electrodes that allow positioning of the electrodes next to or very close to the inner myocardial surface, but are also sufficiently far removed from the nearest adjacent electrode so as to increase the amount of electrical energy that must travel through the myocardium in order to complete the electrical path from one discharge electrode to the other. To achieve a placement sufficiently far enough away has led to placement of the proximal intravascular electrode within the superior vena cava which is outside of the heart above the right atrium. To complete a discharge, a countershock flows from an electrode in the right ventricle up the lateral wall of the right ventricle to the right atrium and into the superior vena cava.

A typical intravascular defibrillation discharge catheter arrangement is seen in U.S. Pat. No. 3,942,536 issued to Mirowski et al. on Mar. 9, 1976, disclosing an intravascular catheter electrode system. The catheter as discussed uses two discharge electrodes separated from each other by at least 1½ inches and up to 4½ inches in order to develop the electrical field needed to effect defibrillation. The catheter system placed a distal electrode at or near the apex of the right ventricle and a proximal electrode outside of the heart proper in the superior vena cava, a large vein draining blood from the upper body into the heart. The concomitant electrical field generated by discharge of current from one electrode to the other would create an approximate ellipsoidal field from the apex of the right ventricle to the superior vena cava with significant amounts of current shunting through the blood within the right atrial and right ventricular chambers.

A second representative electrode system is disclosed in U.S. Pat. No. 4,603,705 issued to Speicher et al. on Aug. 5, 1986. As disclosed, the catheter carries two discharge electrodes. The distal discharge electrode is located near the apex of the right ventricle with a proximal discharge electrode near or in the superior vena cava but no closer than about three inches between the two discharge electrodes. This patent, being similar to the Mirowski patent, recognizes the need to separate the discharge electrodes in an effort to provide a countershock capable of achieving a therapeutic response. The Speicher patent preferred an inter-electrode distance of 4⅓ inches or 11 centimeters.

U.S. Pat. No. 4,817,608 issued to Shapland et al. on Apr. 4, 1989 discussed the Speicher patent and pointed out a deficiency in the Speicher patent by noting that treatment outcome using the Speicher catheter is only 40 to 50% successful even with energy delivered as high as 40 Joules. The Shapland patent discloses a third patch electrode. As disclosed, the reason for adding the third patch electrode is an attempt to expand the electrical field to include more of the myocardium. The method as disclosed electrically connects in common the proximal catheter electrode to the patch electrode and discharges from this electrical combination to the second distal catheter electrode. The catheter inter-electrode distance is in a range from 8 to 14 centimeters or greater than 3 inches. The Shapland patent, however, still suffers from the same deficiency as Mirowski and Speicher because of the closer proximity of the two catheter electrodes by comparison to the distance from the distal catheter electrode to the patch electrode. The vast majority of current will still flow the shorter route having the lower resistance.

These patents, and others, teach that the proximal and distal electrodes mounted on a common catheter must be mounted to maintain an inter-electrode distance of at least 6 centimeters in order to accomplish some cardioversion or defibrillation and avoid excessive and significant shunting or short circuiting between the two electrodes. The distal electrode placed within the right ventricle must be constructed of sufficient size so as to ensure adequate surface area and contact with the inner ventricular wall. There is not adequate consensus as to the actual physical dimensions needed, however, on average the intra-ventricular electrodes are at least 5 centimeters in length. Allowing for an inter-electrode distance of 8 centimeters or 3 inches the proximal electrode is at the most at or near the superior vena cava, a structure outside the heart proper. One effect of this requirement is to force a sub-optimal electrode placement in order to avoid significant short circuiting. A second effect is that the placement of the proximal electrode outside of the heart above the right atrium renders the electrode useless for use in atrial defibrillation. As shown in FIG. 1, the energy that would be delivered to a heart to treat atrial fibrillation or flutter will miss the atria.

SUMMARY OF THE INVENTION

The present invention meets the need for optimal anatomic placement of cardioversion and defibrillation electrodes by providing at least two discharge electrodes mounted on a common intravascular catheter with a distal intra-ventricular electrode having a length and surface area chosen to match the length of the right ventricular wall and a proximal discharge electrode having a length and surface area chosen to match the length and configuration of the right atrial wall, and also utilizing control means within an implantable cardioversion defibrillator (ICD) to prevent countershock current from flowing between these two electrodes. The present invention employs at least one other patch electrode preferably located within the subcutaneous space of the left antero-lateral chest wall such that independent use and control of the distal ventricular electrode and/or proximal atrial electrode will create an electrical field and current path from the right heart wall across the myocardium to at least one subcutaneous patch electrode. Independent control of the intravascular discharge electrodes within the right ventricle and right atrium provides an ICD considerable latitude in treating isolated ventricular dysrhythmias from isolated atrial dysrhythmias to employing both electrodes simultaneously as a third alternative.

Accordingly, it is an aspect of the present invention to provide an ICD capable of utilizing an implantable intravascular catheter that is optimally designed to deliver an efficacious countershock to an ailing human heart. An ICD utilizing the present invention would be capable of controlling a countershock so as to prevent the electrodes mounted on the catheter of the present invention to simultaneously have opposite charge polarity during a countershock.

It is an object of the present invention to provide a more efficacious intravascular discharge electrode catheter for the electrical treatment of cardiac dysrhythmias.

It is an additional object of the present invention to provide an electrode bearing catheter having the feature of conforming to the entire length of the ventricular and atrial walls.

It is a further object of the present invention to provide an entire range of electrode lengths to cover all possible heart conformations allowing the physician implanting the catheter to decide the optimal length for the specific patient.

It is an additional further object of the present invention to provide an effective intravascular catheter electrode suitable for the electrical treatment of atrial and ventricular dysrhythmias.

DETAILED DESCRIPTION

Figure 1:
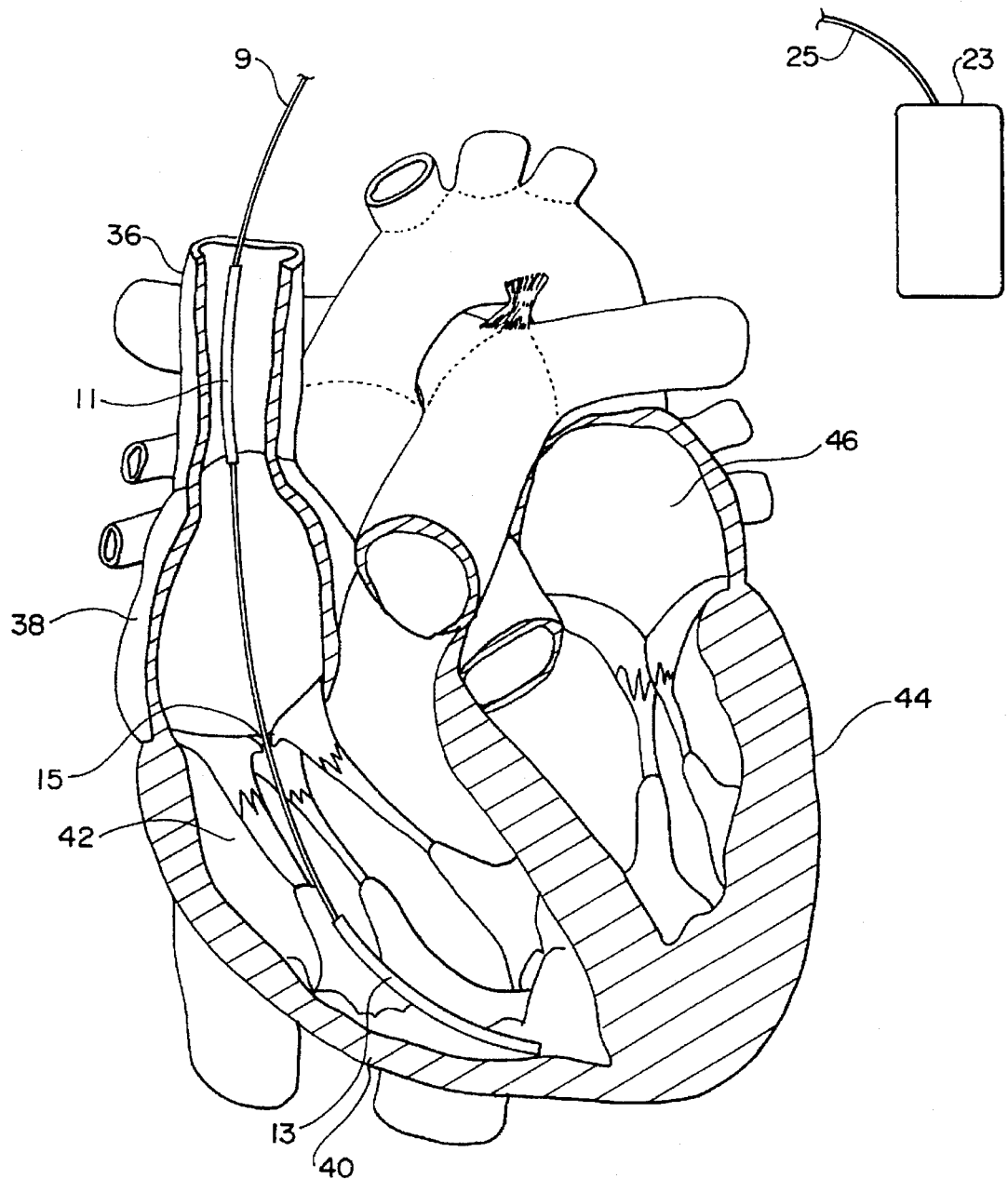
FIG. 1 is a frontal view of a human heart in relative anatomic position depicting the relative position of a prior art catheter and depicting the average result of an electrical field generated by the prior art.

As noted above, FIG. 1 is a general depiction of the prior art placed within a human patient and the prior art is used to independently treat an isolated atrial dysrhythmia. A catheter 9 bearing proximal electrode 11 and distal electrode 13 is positioned in a typical intravascular placement. Proximal electrode I is in the superior vena cava 36 and distal electrode is within the right ventricle 40. A catheter 25, bearing a subcutaneous patch electrode 23 has positioned electrode 23 at the only level possible for the prior art in order to have any possibility to achieve a treatment for an isolated atrial dysrhythmia. As it is, the average electrical field barely includes the superior most aspect of the left atrium 46 and none of the right atrium 38 where the sinus node and the major sino-atrial conduction tracts are located. If patch electrode 23 is any higher, none of the electrical discharge traverses the myocardium. If patch 23 is placed any lower, then the electrical field begins to cross the left ventricular myocardium 44. This is to be avoided because of the substantial risk of causing a fatal ventricular dysrhythmia as a complication in attempting to treat an atrial dysrhythmia. Therefore, the prior art is inadequate for independently treating atrial dysrhythmias.

Figure 2:
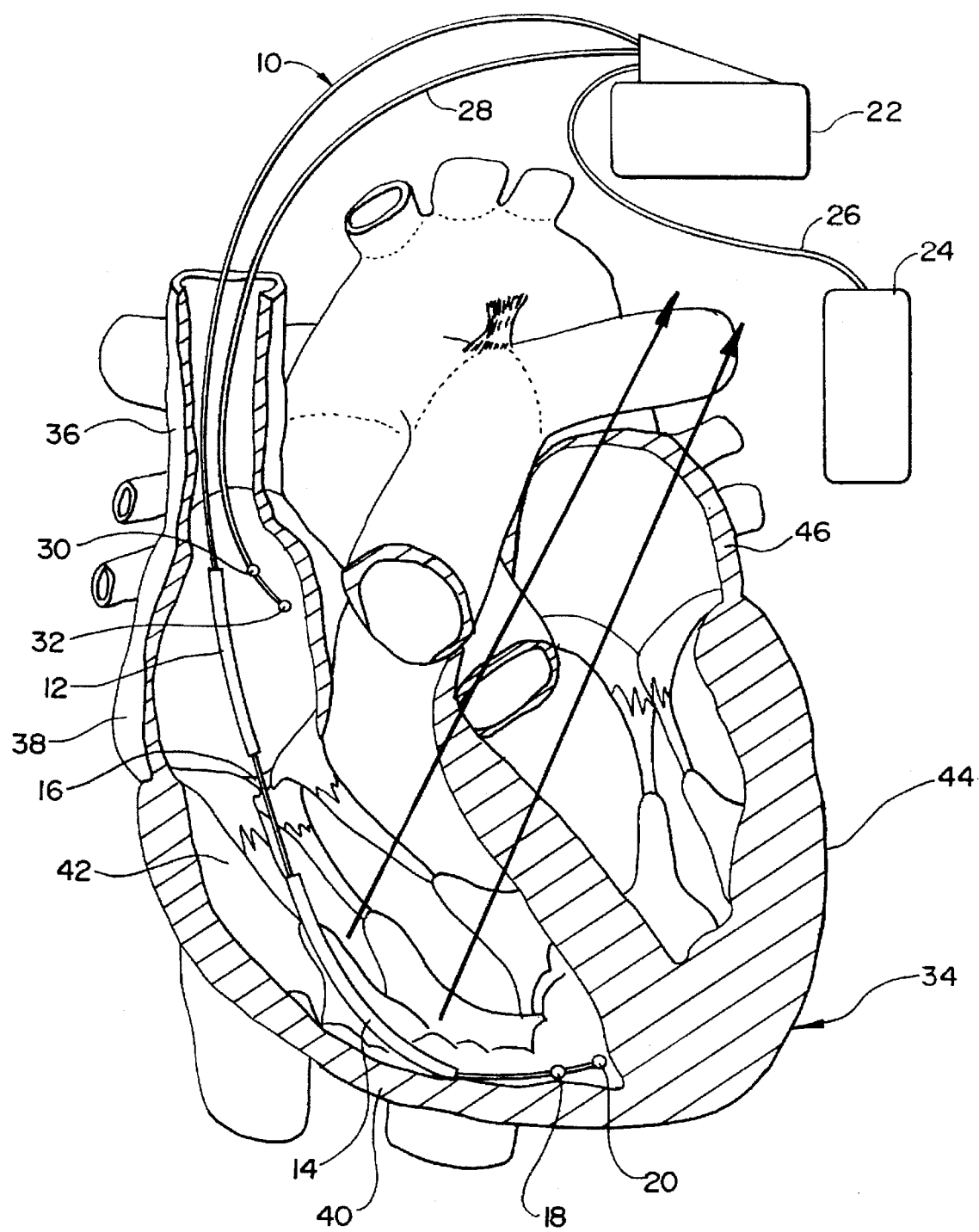
FIG. 2 is a frontal view of a human heart in relative anatomic position depicting the relative position of the present invention and depicting the average result of an electrical field generated by the present invention.

Referring to FIG. 2, there is depicted an embodiment of the present invention comprising catheter 10 bearing proximal discharge electrode 12 and distal discharge electrode 14, which are separated by interelectrode space 16; proximal sensing electrode 18, and distal sensing electrode 20. Each of these four electrodes mounted on catheter 10 are electrically connected through independent wire leads within catheter 10 to an automatic implantable cardioverter defibrillator (ICD) 22 which is also electrically connected to subcutaneous patch electrode 24 via catheter lead 26. A third catheter 28 is shown bearing proximal sensing electrode 30 and distal sensing electrode 32 for sensing atrial dysrhythmia.

ICD 22, patch electrode 24 and intravascular sensing catheter 28 are known in the art. ICD 22 is programmed to sense a dysrhythmic condition within the heart and in response ICD 22 will provide cardioverting or defibrillating electrical countershocks to the heart through the implantable electrodes. A preferred implantation site for patch electrode 24 is within the subcutaneous space in a left antero-lateral position on the chest wall. The metallic housing of ICD 22 can likewise be electrically connected so as to provide an electrode surface suitable to act as an additional discharge electrode implanted at a second subcutaneous site provided ICD 22 is capable of subcutaneous implantation in the pectoral region. Catheters 10 and 28 gain access to a human heart 34 through intravenous implantation, ideally utilizing a subclavian vein, not depicted, and threading catheters 10 and 28 along the venous return through the superior vena-cava 36 and into right atrium 38 and right ventricle 40 traversing the tricuspid valve opening 42.

Referring to FIG. 2, it can be seen that electrode bearing catheter 10 is a flexible structure bearing four independent electrodes that includes sensing electrodes 18 and 20 residing at the distal end of catheter 10 with distal sensing electrode 20 consisting of a metallic cap or ring having a surface area of approximately 10–50 mm$^2$ with proximal sensing electrode 18 spaced from 1–5 mm proximal to sensing electrode 20 and typically having a structure such as a metallic ring electrode with a surface area of approximately 10 to 50 mm$^2$. Discharge electrode 14 is typically formed out of a conductive spring electrode material usually of drawn braised strand wire coiled about the surface of catheter 10. The conductive wire is preferably close wound to achieve a uniform discharge surface but retaining flexibility. The final length of electrode 14 is dependent upon the actual size of right ventricle 40. The present invention eliminates any need to restrain the working length of electrode 14 and an optimal fit can be determined by performing simple measurement steps to determine the optimum length for electrode 14 based on the length of right ventricle 40. As shown in FIG. 2, the proximal end of electrode 14 ends at the tricuspid valve annulus defining tricuspid valve opening 42. Proper placement of electrode 14 is achieved when distal sensing electrode 20 has been placed at the apex of right ventricle 40.

Proximal discharge electrode 12 is of similar construction to discharge electrode 14 with its length chosen to conform with the actual measurement of right atrium 38. The present invention allows proximal discharge electrode 12 to obtain sufficient length so as to maximize the useable surface area of proximal discharge electrode 12. It is anticipated by the present invention that proximal discharge electrode 12 may be constructed to achieve a length in excess of the atrial wall length and extend out into the superior vena cava. The decision on whether to use the longer electrode is left to the physician and the individual need of the patient. Alternative electrode construction for discharge electrodes 12 and 14 consists of utilizing a series of solid metal rings electrically wired together to achieve the conformation and length necessary to optimally utilize positioning within the right atrium 38 or right ventricle 40 respectively.

The present invention allows for independent utilization of discharge electrodes 12 and 14 such that electrode inner space 16 is of a variable distance which can be as small as a fraction of a millimeter to as great as 5 centimeters and still achieve optimum anatomical positioning within the right ventricle and atrium. Discharge electrode 14 could be of sufficient length to extend from the right ventricular apex up to and across the tricuspid valve as a means for optimizing electrode configuration for the patient's needs.

FIG. 2 depicts proximal discharge electrode 12 having a length conforming to the length of right atrium 38. The present invention allows for discharge electrode 12 to be of any useful length extending from the proximal end of discharge electrode 14 on up and out into the area of the superior vena cava 36. The choice of length for discharge electrodes 12 and 14 is predicated on anatomic as well as functional considerations as shown and considered by the physician implanting the device.

In operation, distal sensing electrodes 18 and 20 and proximal sensing electrodes 30 and 32 are utilized by ICD 22 to sense and detect cardiac dysrhythmia in both the ventricles and atria. As shown in FIG. 2, discharge of a countershock between discharge electrode 14 and the housing electrode of ICD 22 creates an electrical field that well encompasses right ventricle 40 and left ventricle 44. The artatomic positioning of left atrium 46, shown here in phantom relief, is lying outside the electrical field generated by a countershock discharge between discharge electrode 14 and housing electrode of ICD 22.

Figure 3:
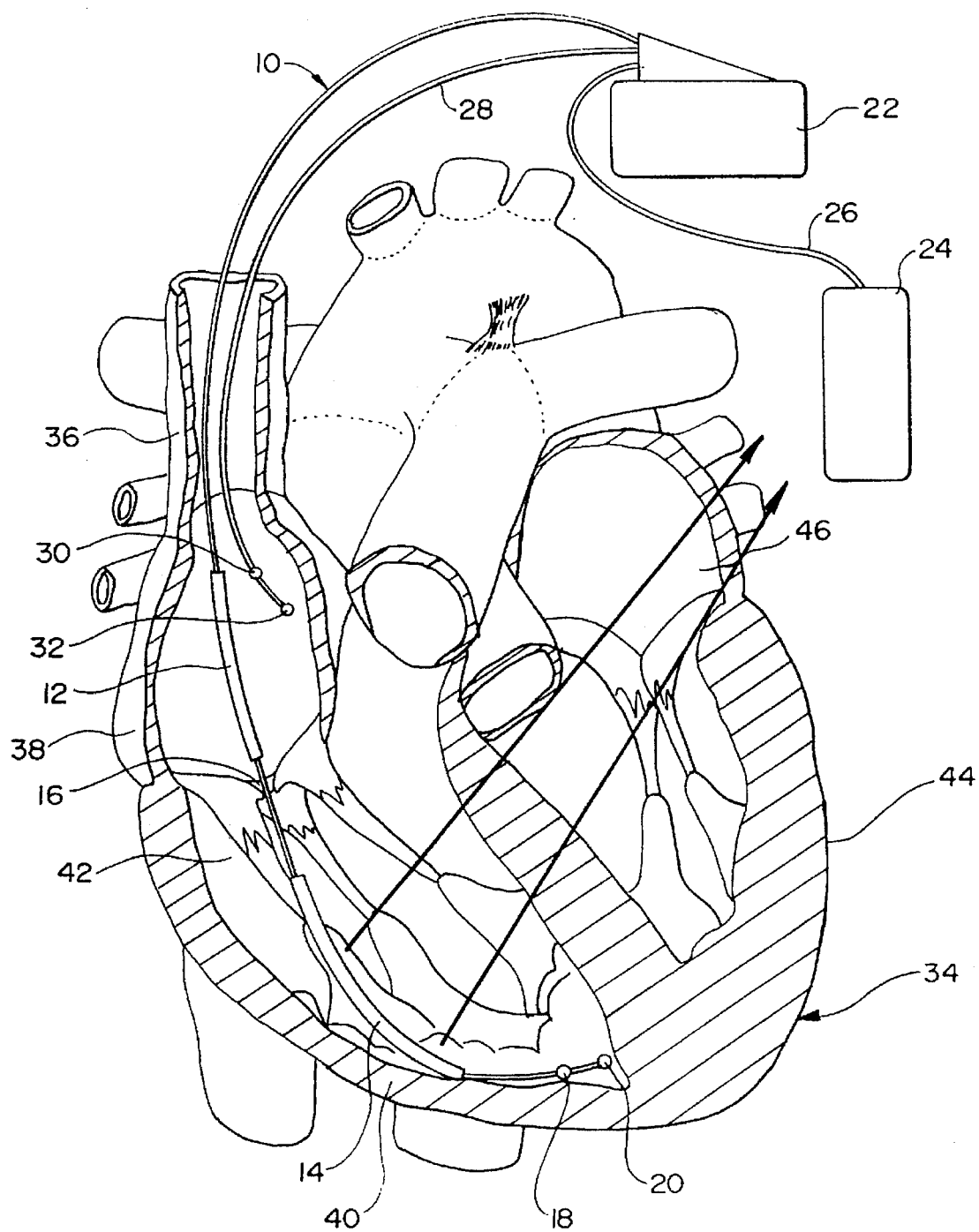
FIG. 3 is a frontal view of a human heart in relative anatomic position depicting the relative position of the present invention and depicting the average result of an electrical field generated by the present invention.

FIG. 3 depicts an alternative operating modality for treatment of a sensed ventricular dysrhythmia utilizing a countershock discharge between distal discharge electrode 14 and subcutaneous patch electrode 24. As shown in FIG. 3, the optimized length of distal discharge electrode 14 allows for maximized envelopment of right ventricle 40 and left ventricle 44 within the electrical field of the countershock discharge.

Figure 4:
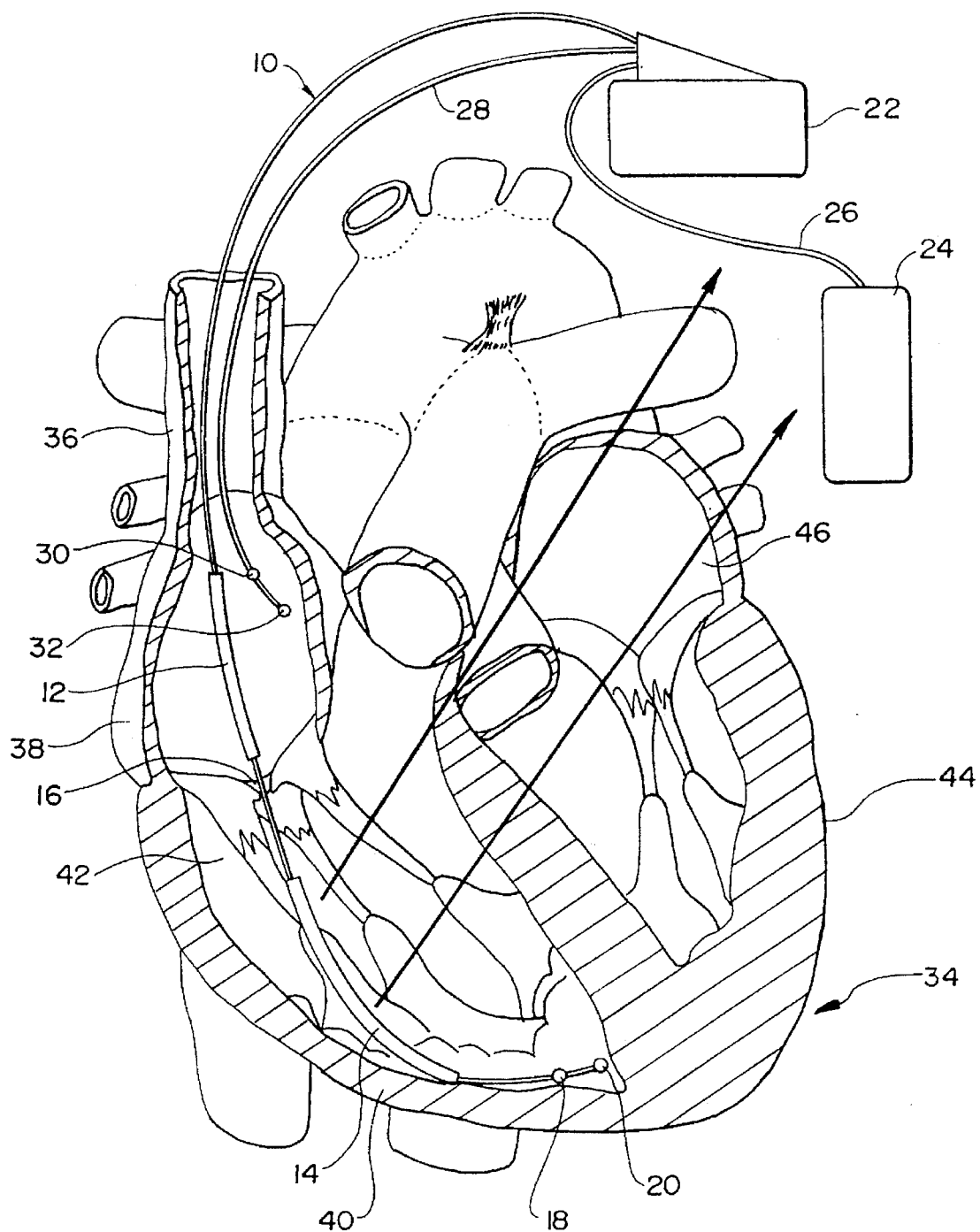
FIG. 4 is a frontal view of a human heart in relative anatomic position depicting the relative position of the present invention and depicting the average result of an electrical field generated by the present invention.

FIG. 4 depicts a third alternate operation where the electrical countershock discharge is spaced out between distal countershock electrode 14 and subcutaneous patch electrode 24 and the housing electrode of ICD 22, the electrical field generated in this fashion would dilute out the charge density through the myocardium, but would provide a large and useful electrical field fully encompassing the right and left ventricles.

Figure 5:
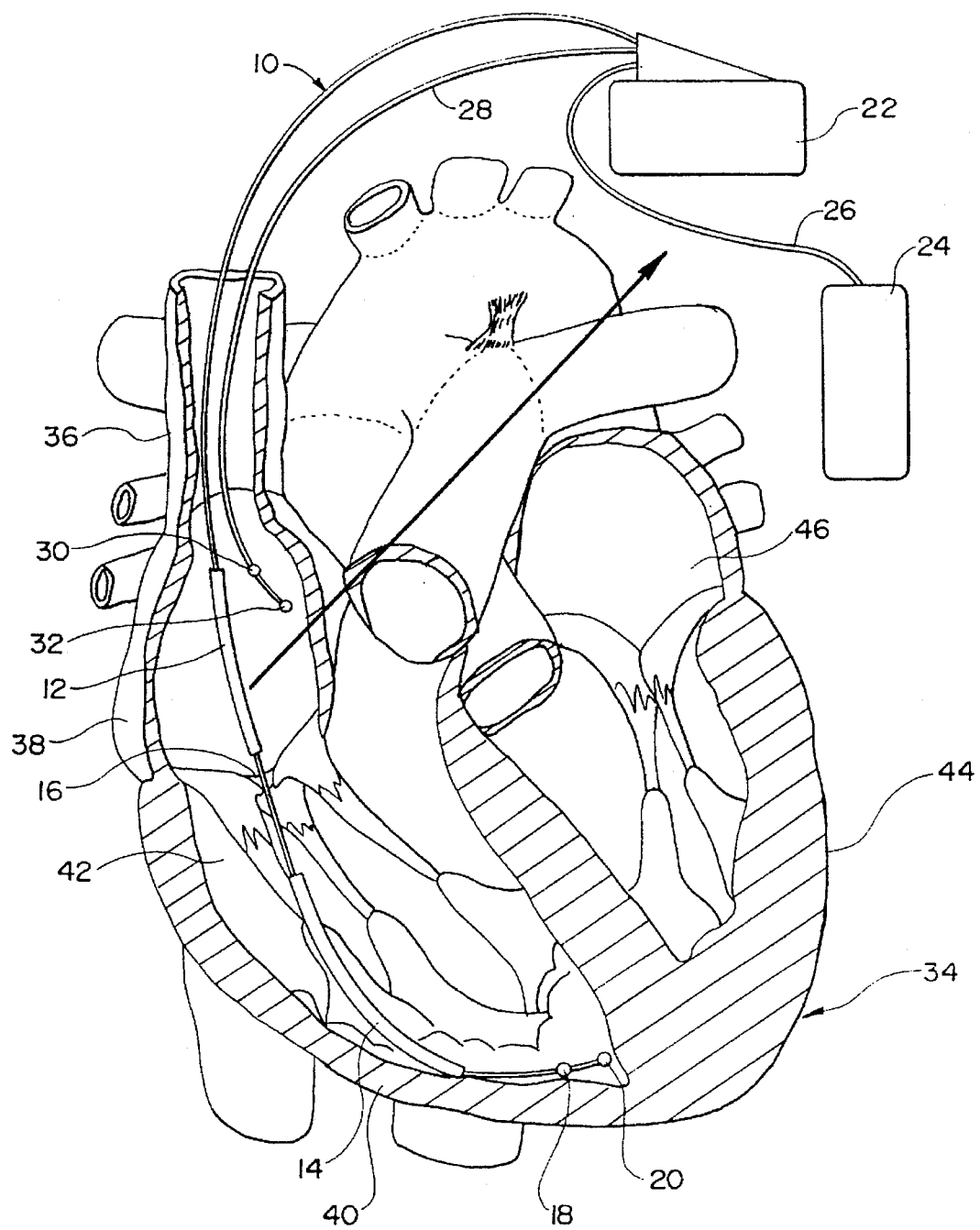
FIG. 5 is a frontal view of a human heart in relative anatomic position depicting the relative position of the present invention and depicting the average result of an electrical field generated by the present invention.

FIG. 5 depicts the operation of proximal discharge electrode 12 discharging to the discharge electrode housing of ICD 22. As shown, the electrical field traverses right atrium 38 and left atrium 46. This electrical field is useful for treatment of cardiac dysrhythmia isolated to the atria and sensed via sensing electrodes 30 and 32.

Figure 6:
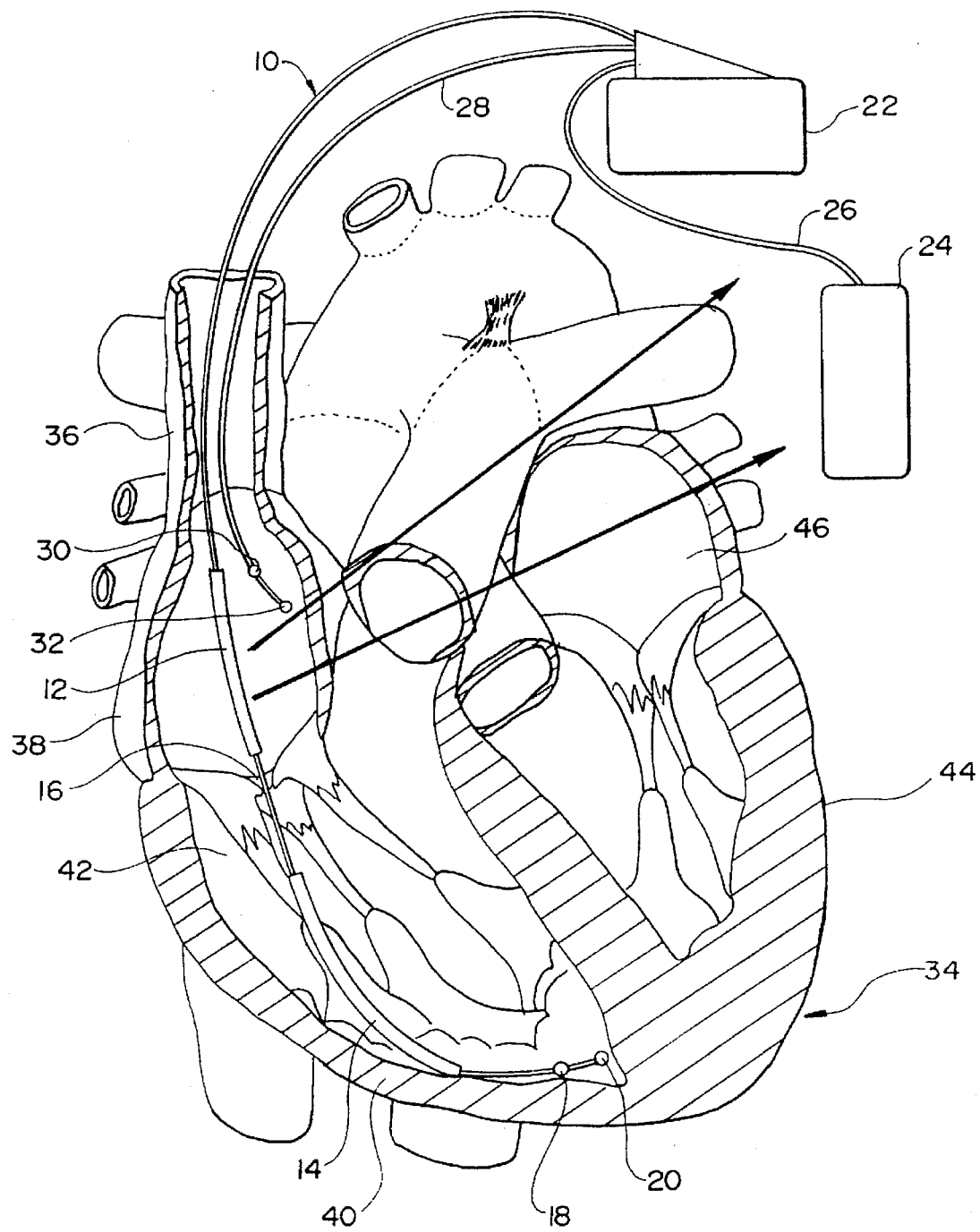
FIG. 6 is a frontal view of a human heart in relative anatomic position depicting the relative position of the present invention and depicting the average result of an electrical field generated by the present invention.

FIG. 6 depicts the operational use of proximal discharge electrode 12 and both housing electrode of ICD 22 and subcutaneous patch electrode 24 to generate a countershock discharge through a larger volume of myocardium but still essentially focused through right atrium 38 and left atrium 46. A third alternative use of proximal discharge electrode 12, not depicted in any figure, would be a delivery of a countershock discharge between proximal discharge electrode 12 and subcutaneous patch electrode 24.

Figure 7:
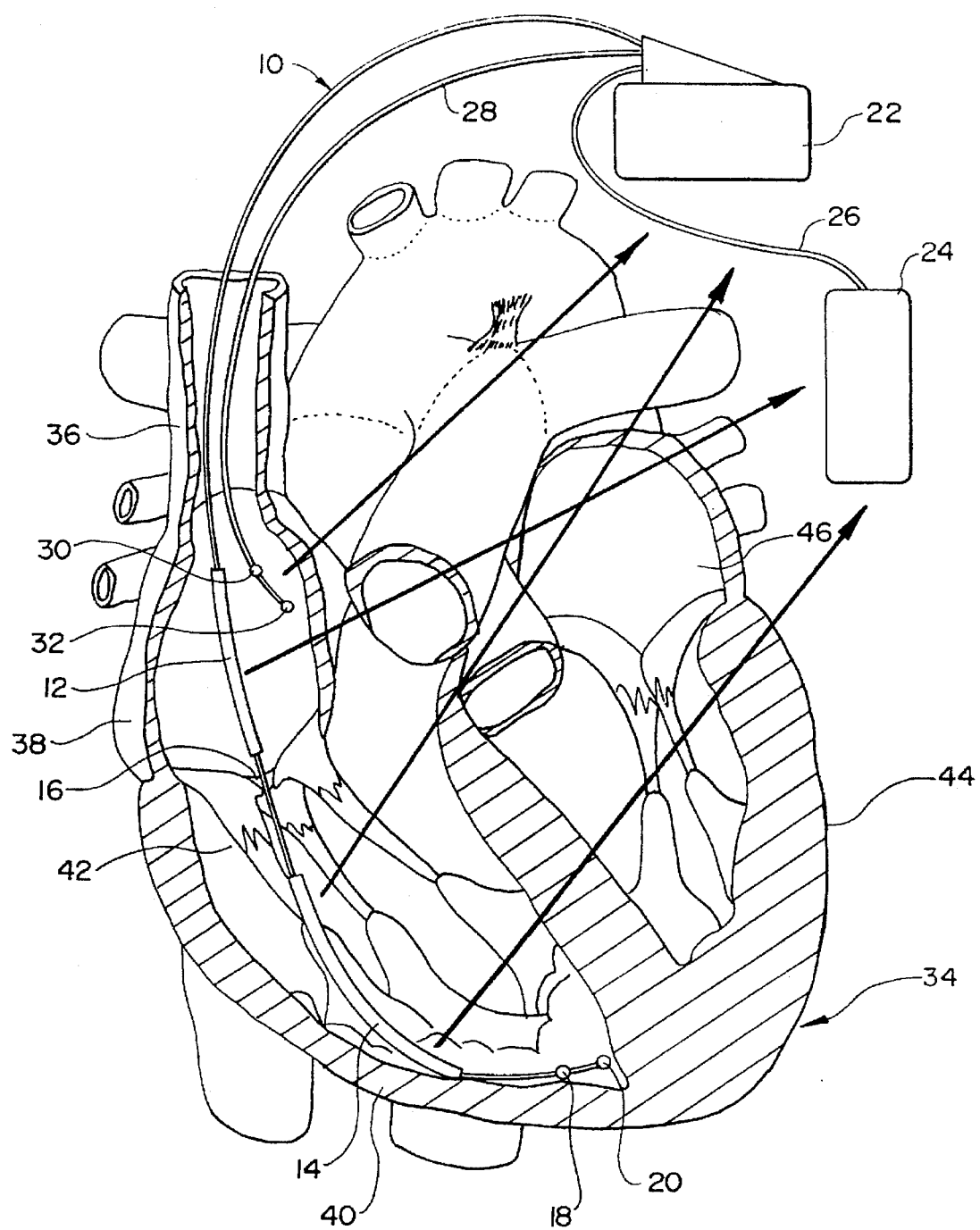
FIG. 7 is a frontal view of a human heart in relative anatomic position depicting the relative position of the present invention and depicting the average result of an electrical field generated by the present invention.

The present invention, as depicted in FIG. 7, shows the simultaneous use of proximal discharge electrode 12 and distal discharge electrode 14 generating an electrical field between electrodes 12 and 14 and housing electrode of ICD 22 and subcutaneous patch electrode 24. The electrical field generated by this operation is sufficiently large to encompass the entire myocardium and traverse the myocardium from one side to the other.

A preferred embodiment of the present invention provides control to the discharge pathways by using independently controllable electrode discharge pathways as disclosed in co-pending U.S. patent application entitled IMPLANTABLE CARDIOVERTER DEFIBRILLATOR SYSTEM HAVING INDEPENDENTLY CONTROLLABLE ELECTRODE DISCHARGE PATHWAY, Ser. No. 08/096,170, filed Jul. 22, 1993, and assigned to the same assignee of the present invention, a copy of which is attached and the disclosure of which is hereby incorporated by reference. Alternatively, appropriate countershock sequence can be hardwired within an ICD to prevent countershock discharge from traversing between the proximal and distal discharge electrodes.

A preferred embodiment of construction is disclosed in co-pending U.S. Patent Application entitled LOW PROFILE DEFIBRILLATION CATHETER, Ser. No. 07/919,233, Jul. 7, 1992 and assigned to the same assignee of the present invention, a copy of which is attached and the disclosure of which is hereby incorporated by reference.

I claim:

1. An improved implantable system for producing a countershock for electrically cardioverting a human patient's heart, the implantable system being a self-contained human implantable device including a charge storage means, and means for selectively discharging the electrical charge in the charge storage means as a countershock to be delivered through electrodes implanted in the human patient in response to a sensing of a myocardial arrhythmia in the human patient, the improvement comprising:

a) discharge electrode means electrically connected to the charge storage means for electrically cardioverting the human patient's heart upon a discharge of said charge storage means, the discharge electrode means including at least one implanted intravascular catheter carrying a first and second discharge electrodes axially spaced apart on the catheter by no more than 5 cm to effect appropriate anatomic positions of the first and second electrodes within the atrium and the ventricle respectively of the human patient's heart; and b) control means as part of the means for selectively discharging for controlling a polarity of the discharge of the charge storage means to ensure that the first and second discharge electrodes are not simultaneously discharged in an opposite polarity at any time during the discharge of the charge storage means.

2. The system of claim 1 in which the discharge electrode means comprises a subcutaneous patch electrode and an intravascular catheter bearing two or more discharge electrodes of which one catheter borne electrode is placed substantially within the right atrium so that the subcutaneous patch electrode and the right atrial discharge electrode are capable of independently electrically cardioverting the human patient's heart suffering from atrial dysrhythmia.

3. The system of claim 1 in which the discharge electrode means comprises a pulse generator housing subcutaneous electrode and an intravascular catheter bearing two or more discharge electrodes of which one catheter borne electrode is placed substantially within the right atrium so that the pulse generator housing subcutaneous electrode and the right atrial discharge electrode are capable of independently electrically cardioverting the human patient's heart suffering from atrial dysrhythmia.

4. The system of claim 1 in which the control means comprises means for controlling the discharge phase, duration, and direction.

5. A method for operating an implantable device for electrically cardioverting a human heart to treat myocardial dysrhythmia, the method comprising the steps of:

a) implanting an intravascular catheter within the human heart carrying at least two discharge electrodes axially spaced apart less than 5 cm from one another;

b) implanting proximate the human heart one or more additional discharge electrodes;

c) implanting a cardioverting system;

d) electrically connecting the intravascular catheter and the one or more additional discharge electrodes to the implanted cardioverting system;

e) using the cardioverting system to perform the device-implemented steps of:

e2) sensing for myocardial dysrhythmia amenable to electrical cardioverting by the cardioverting system;

e2) discharging the cardioverting system in response to sensing a myocardial dysrhythmia; and e3) controlling a polarity of an electrical discharge of the cardioverting system to prevent the at least two electrodes of the intravascular catheter from simultaneously having opposite polarity at any time during the electrical discharge.

6. The method of claim 6 in which the controlling step comprises controlling the discharge phase, duration, and direction.

7. An improved implantable intravascular catheter having at least two electrical discharge electrodes spaced for appropriate anatomic positioning within a human heart for independent atrial and ventricular defibrillation, the improved catheter comprising:

a proximal first discharge electrode located on the catheter, positionable within the right atrium of the human heart, and capable of delivering an electrical countershock of greater than about 1.0 Joules; and a distal second discharge electrode located on the catheter, positionable within the right ventricle of the human heart, and capable of delivering an electrical countershock of greater than about 1.0 Joules, the distal second discharge electrode being optimally spaced apart from the proximal first discharge electrode by no more than 5 cm.

* * * * *